(12) United States Patent
Lavitrano et al.

(10) Patent No.: US 8,889,643 B2
(45) Date of Patent: Nov. 18, 2014

(54) ISOFORM OF BRUTON'S TYROSINE KINASE (BTK) PROTEIN

(75) Inventors: Marialuisa Lavitrano, Milan (IT); Emanuela Grassilli, Monza (IT); Kristian Helin, Charlottenlund (DK)

(73) Assignee: Bionsil, S.r.l., Milan (IT)

( * ) Notice: Subject to any disclaimer, the term of this patent is extended or adjusted under 35 U.S.C. 154(b) by 0 days.

(21) Appl. No.: 13/532,680

(22) Filed: Jun. 25, 2012

(65) Prior Publication Data
US 2013/0041014 A1 Feb. 14, 2013

Related U.S. Application Data

(62) Division of application No. 12/531,061, filed as application No. PCT/EP2008/053099 on Mar. 14, 2008, now Pat. No. 8,232,085.

(30) Foreign Application Priority Data

Mar. 14, 2007 (IT) .............................. PD2007A0088
Apr. 13, 2007 (EP) .................................... 07106119

(51) Int. Cl.
*A61K 48/00* (2006.01)
*C07H 21/02* (2006.01)
*C07H 21/04* (2006.01)
*C12N 15/63* (2006.01)

(52) U.S. Cl.
USPC ......... 514/44; 536/23.1; 536/24.5; 435/320.1

(58) Field of Classification Search
None
See application file for complete search history.

(56) References Cited

U.S. PATENT DOCUMENTS

| | | | |
|---|---|---|---|
| 6,303,652 B1 | 10/2001 | Uckun et al. | |
| 6,548,272 B1 | 4/2003 | Shimizu et al. | |
| 2002/0086838 A1 | 7/2002 | Oh et al. | |
| 2002/0178459 A1 | 11/2002 | McNeish et al. | |
| 2005/0107386 A1 | 5/2005 | Narla et al. | |
| 2005/0246794 A1 | 11/2005 | Khvorova et al. | |
| 2005/0266561 A1 | 12/2005 | Wells | |
| 2006/0292153 A1* | 12/2006 | Benayahu et al. | 424/146.1 |
| 2007/0244312 A1 | 10/2007 | Khvorova et al. | |
| 2007/0275465 A1 | 11/2007 | Woppmann et al. | |
| 2008/0014583 A1 | 1/2008 | Montminy et al. | |
| 2008/0108583 A1 | 5/2008 | Feinstein | |
| 2009/0221679 A1 | 9/2009 | Espeseth et al. | |

FOREIGN PATENT DOCUMENTS

| | | |
|---|---|---|
| EP | 1662259 | 5/2006 |
| WO | 0238797 | 5/2002 |
| WO | 2005056766 | 6/2005 |
| WO | 2006041902 | 4/2006 |
| WO | 2006063164 | 6/2006 |
| WO | 2006081418 | 8/2006 |
| WO | 2006113679 | 10/2006 |

OTHER PUBLICATIONS

Scherer et al. (Nat. Biotechnol., 2003, 21(12), pp. 1457-1465).*
Zhang et al. (Current Pharmaceutical Biotechnology 2004, vol. 5, p. 1-7).*
Bertrand et al. (Biochemical and Biophysical Research Communications, 296, 2002, 1000-1004).*
Bartz Steven R et al: "Small Interfering RNA Screens Reveal Enhanced Cisplatin Cytotoxicity in Tumor Cells Having Both BRCA Network and TP53 Disruptions" Molecular and Cellular Biology, American Society for Microbiology, Washington, US, vol. 26, No. 24, Dec. 1, 2006, pp. 9377-9386, XP009077057 ISSN: 0270-7306.
Levin P A et al: "Liposomal delivery of EphA2 siRNA in combination with gemcitabine reduces pancreatic tumor growth and invasion" Pancreas, vol. 33, No. 4, Nov. 2006, p. 477, XP002502047 & 37th Annual Meeting of the American-Pancreatic-Association/13th Meeting of the International-Associa; Chicago, IL, USA; Nov. 1-4, 2006 ISSN: 0885-3177.
Landen Charles N Jr et al: "Therapeutic EphA2 gene targeting in vivo using neutral liposomal small interfering RNA delivery" Cancer Research, vol. 65, No. 15, Aug. 2005, pp. 6910-6918, XP002502048 ISSN: 0008-5472.
Mao Weiguang et al: "EphB2 as a therapeutic antibody drug target for the treatment of colorectal cancer" Cancer Research, American Association for Cancer Research, Baltimore, USA, DE, vol. 64, No. 3, Feb. 1, 2004, pp. 781-788, XP002343724.
Shakoori et al: "Deregulated GSK3beta activity in colorectal cancer: Its association with tumor cell survival and proliferation" Biochemical and Biophysical Research Communications, Academic Press Inc. Orlando, FL, US, vol. 334, No. 4, Sep. 9, 2005, pp. 1365-1373, XP005001539 ISSN: 0006-291X.
De Toni F et al: "A crosstalk between the Wnt and the adhesion-dependent signaling pathways governs the chemosensitivity of acute myeloid leukemia" Oncogene, vol. 25, No. 22, May 2006, pp. 3113-3122, XP002502049 ISSN: 0950-9232.

(Continued)

*Primary Examiner* — Amy Bowman
(74) *Attorney, Agent, or Firm* — Beverly W. Lubit (57) ABSTRACT

The use of compounds is described which are capable of functionally blocking at least one of the genes chosen from the group composed of EphAI, EphA2, EphA8, EphB2, CSF1R, VEGFR2, RAMP2, RAMP3, CLRN1, MAPK4, PIK3C2A, PIK3CG, GSK3alpha, GSK3beta, IRAK3, DAPK1, JAK1, PIM1, TRB3, BTG1, LATS1, LIMK2, MYLK, PAK1, PAK2, CDC2, BTK, PNRC2, NCOA4, NR2C1, TPR, RBBP8, TRPC7, FXYD1, ERNI, PRSS16, RPS3, CCL23 and SERPINE1, for the manufacture of a medicament destined to diminish the resistance to chemotherapeutic drugs in the therapeutic treatment of epithelial tumor pathologies. Also described is a method for the determination of the drug resistance in tumor cells, as well as a method for the identification of tumor stem cells.

10 Claims, 7 Drawing Sheets

(56) References Cited

OTHER PUBLICATIONS

Tan Jing et al: "Pharmacologic modulation of glycogen synthase kinase-3 beta promotes p53-dependent apoptosis through a direct bax-mediated mitochondrial pathway in colorectal cancer cells" Cancer Research, vol. 65, No. 19, Oct. 2005, pp. 9012-9020,8993, XP002502050 ISSN: 0008-5472.

Uckun Fatih M et al: "In vivo pharmacokinetic features, toxicity profile, and chemosensitizing activity of alpha-cyano-beta-hydroxy-beta- methyl-N-(2,5-dibromophenyl)propenamide (LFM-A13), a novel anti leukemic agent targeting Bruton's tyrosine kinase." Clinical Cancer Research: An Official Journal of the American Association for Cancer Research May 2002, vol. 8, No. 5, May 2002, pp. 1224-1233, XP002502051 ISSN: 1078-0432.

Uckun et al: "Anti-breast cancer activity of LFM-A13, a potent inhibitor of Polo-like kinase (PLK)" Bioorganic & Medicinal Chemistry, Elsevier Science Ltd, GB, vol. 15, No. 2, Dec. 12, 2006, pp. 800-814, XP005882800 ISSN: 0968-0896.

"Colorectal Cancer" The Merck Manual, [Online] Dec. 2007, pp. 1-5, XP002502052 Retrieved from the Internet: URL:http://www.merck.com/mmpe/print/sec02/ch021/ch021h.html> [retrieved on Oct. 20, 2008].

"Modalities of Cancer Therapy" The Merck Manual, [Online] Nov. 2005, pp. 1-6, XP002502053 Retrieved from the Internet: URL:http://www.merck.com/mmpe/print/sec11/ch149/ch149b.html> [retrieved on Oct. 30, 2008].

Hafner C et al: "Expression profile of Eph receptors and ephrin ligands in human skin and downregulation of EphA1 in nonmelanoma skin cancer" Modern Pathology 20061021 GB, vol. 19, No. 10, Oct. 21, 2006, pp. 1369-1377, XP002487739 ISSN: 0893-3952 1530-0285.

Masuda Junko et al: "Fibronectin type I repeat is a nonactivating ligand for EphA1 and inhibits ATF3-dependent angiogenesis." The Journal of Biological Chemistry May 9, 2008, vol. 283, No. 19, May 9, 2008, pp. 13148-13155, XP002487740 ISSN: 0021-9258.

Surawska H et al: "The role of ephrins and Eph receptors in cancer" Cytokine and Growth Factor Reviews, Oxford, GB, vol. 15, No. 6, Dec. 1, 2004, pp. 419-433, XP004652022 ISSN: 1359-6101.

Afar et al., "Regulation of Btk by Src family tyrosine kinases," Molecular and Cellular Biology, Jul. 1996, vol. 16, No. 7, pp. 3465-3471.

Hebert, M. D., "Phosphorylation and the Cajal body: modification in search of function," Archives of Biochemistry and Biophysics, vol. 496, No. 2, 2010, pp. 69-76.

Lowry, W. E. et al., "Role of the PHTH Module in Protein Substrate Recognition by Bruton's Agammaglobulinemia Tyrosine Kinase ," J. Biol. Chem., 2001, vol. 276, pp. 45276-45281.

Rawlings, D. J. et al., "Mutation of unique region of Bruton's tyrosine kinase in immunodeficient XID mice," Science, vol. 261, Jul. 16, 1993, pp. 358-361.

Suzuki, H. et al., "PI3K and BTK differentially regulate B cell antigen receptor-mediated signal transduction," vol. 4, No. 3, Mar. 2003, pp. 280-286.

Tsai, Y. -T. et al., "Etk, a Btk Family Tyrosine Kinase, Mediates Cellular Transformation by Linking SRC to STAT3 Activation," Mol. Cell. Biol., 2000, vol. 20, No. 6, pp. 2043-2054.

Okoh, M. P. et al., "Pleckstrin Homology Domains of Tec Family Protein Kinases," Biochemical and Biophysical Research Communications, vol. 265, No. 1, Nov. 11, 1999, pp. 151-157.

Chica, R. A. et al., "Semi-rational approaches to engineering enzyme activity: combining the benefits of directed evolution and rational design," Current Opinion in Biotechnology, 2005, vol. 16, No. 4, pp. 378-384.

Sen, S. et al., "Developments in directed evolution for improving enzyme functions," Appl. Biochem. Biotechnol., 143: 212-223 (2007).

National Center for Biotechnology Information (NCBI) Protein Database, Accession No. Q06187, Human-BTK, Published Jun. 1, 1994.

National Center for Biotechnology Information (NCBI) Protein Database, Accession No. P35991, Mouse-BTK, Published Jun. 1, 1994.

Berns, K. et al., "A large-scale RNAi screen in human cells identifies new components of the p53 pathway," Nature, 428: 431-437 (2004).

* cited by examiner

```
CLUSTAL 2.0.3 multiple sequence alignment
```

SEQ ID NO: 6  NM_000061    ------------------------------------------------------------
              alternative  TTTTGGTGGACTCTGCTACGTAGTGGCGTTCAGTGAAGGGAGCAGTGTTTTTCCCAGATC  60

SEQ ID NO: 6  NM_000061    ------------------------------------------------------------
              alternative  CTCTGGCCTCCCCGTCCCCGAGGGAAGCCAGGACTAGGGTCGAATGAAGGGGTCCTCCAC  120

SEQ ID NO: 6  NM_000061    ------------------------------------------------CTCAGACTG  9
              alternative  CTCCACGTTCCATTCCTGTTCCACCTCAAGGTCACTGGGAACACCTTTCGCAGCAAACTG  180
                                                                            **

SEQ ID NO: 6  NM_000061    TCCTTCCTCTCTGGACTGTAAGAATATGTCTCCAGGGCCAGT--GTCTGCTGCG-ATCGA  66
              alternative  ---CTAATTCAATGAAGACCTGGAGGGAGCCAATTGTTCCAGTTCATCTATCACATGGCCA  238
                                  ** *      **    *  *   *  ***  *   *    *  *

SEQ ID NO: 6  NM_000061    GTCCCACCTTCCAAGTCCTGGCATCTCAATGCATCTGGGAAGCTACCTGCATTAAGTCAG  126
              alternative  GTTGGTCCATTCAACAAATGGTTATTGGATGC--CCATTATGTGGCAGGCACTGTTCCGG  296
                                 *  ***    * * **     *** * *  ***  *   * *

SEQ ID NO: 6  NM_000061    GACT GAGCACACAGGTGAACTCCAGAAAGAAGAAGCTATGGCCGCAGTGATTCTGGAGAG  186
              alternative  GGGA GAGCACACAGGTGAACTCCAGAAAGAAGAAGCTATGGCCGCAGTGATTCTGGAGAG  356
                             * ************************************************

SEQUENCE LISTING

<160> NUMBER OF SEQ ID NOS: 6

<210> SEQ ID NO 1
<211> LENGTH: 300
<212> TYPE: DNA
<213> ORGANISM: Homo sapiens

<400> SEQUENCE: 1
ttttggtgga ctctgctacg tagtggcgtt cagtgaaggg agcagtgttt ttcccagatc    60
ctctggcctc cccgtccccg agggaagcca ggactagggt cgaatgaagg ggtcctccac   120
ctccacgttc cattcctgtt ccacctcaag gtcactggga acacctttcg cagcaaactg   180
ctaattcaat gaagacctgg agggagccaa ttgttccagt tcatctatca catggccagt   240
tggtccattc aacaaatggt tattggatgc ccattatgtg gcaggcactg ttccggggga   300

<210> SEQ ID NO 2
<211> LENGTH: 571
<212> TYPE: PRT
<213> ORGANISM: Homo sapiens

<400> SEQUENCE: 2

Met Glu Gln Ile Ser Ile Ile Glu Arg Phe Pro Tyr Pro Phe Gln Val
1               5                   10                  15

Val Tyr Asp Glu Gly Pro Leu Tyr Val Phe Ser Pro Thr Glu Glu Leu
            20                  25                  30

Arg Lys Arg Trp Ile His Gln Leu Lys Asn Val Ile Arg Tyr Asn Ser
        35                  40                  45

Asp Leu Val Gln Lys Tyr His Pro Cys Phe Trp Ile Asp Gly Gln Tyr
    50                  55                  60

Leu Cys Cys Ser Gln Thr Ala Lys Asn Ala Met Gly Cys Gln Ile Leu
65                  70                  75                  80

Glu Asn Arg Asn Gly Ser Leu Lys Pro Gly Ser His Arg Lys Thr
                85                  90                  95

Lys Lys Pro Leu Pro Pro Thr Pro Glu Glu Asp Gln Ile Leu Lys Lys
            100                 105                 110

Pro Leu Pro Pro Glu Pro Ala Ala Ala Pro Val Ser Thr Ser Glu Leu
        115                 120                 125

Lys Lys Val Val Ala Leu Tyr Asp Tyr Met Pro Met Asn Ala Asn Asp
    130                 135                 140

Leu Gln Leu Arg Lys Gly Asp Glu Tyr Phe Ile Leu Glu Glu Ser Asn
145                 150                 155                 160

Leu Pro Trp Trp Arg Ala Arg Asp Lys Asn Gly Gln Glu Gly Tyr Ile
                165                 170                 175

Pro Ser Asn Tyr Val Thr Glu Ala Glu Asp Ser Ile Glu Met Tyr Glu
            180                 185                 190

Trp Tyr Ser Lys His Met Thr Arg Ser Gln Ala Glu Gln Leu Leu Lys
        195                 200                 205

Gln Glu Gly Lys Glu Gly Gly Phe Ile Val Arg Asp Ser Ser Lys Ala
    210                 215                 220

Gly Lys Tyr Thr Val Ser Val Phe Ala Lys Ser Thr Gly Asp Pro Gln
225                 230                 235                 240

Gly Val Ile Arg His Tyr Val Val Cys Ser Thr Pro Gln Ser Gln Tyr
                245                 250                 255

Tyr Leu Ala Glu Lys His Leu Phe Ser Thr Ile Pro Glu Leu Ile Asn
            260                 265                 270

```
Tyr His Gln His Asn Ser Ala Gly Leu Ile Ser Arg Leu Lys Tyr Pro
            275                 280                 285

Val Ser Gln Gln Asn Lys Asn Ala Pro Ser Thr Ala Gly Leu Gly Tyr
290                 295                 300

Gly Ser Trp Glu Ile Asp Pro Lys Asp Leu Thr Phe Leu Lys Glu Leu
305                 310                 315                 320

Gly Thr Gly Gln Phe Gly Val Val Lys Tyr Gly Lys Trp Arg Gly Gln
                325                 330                 335

Tyr Asp Val Ala Ile Lys Met Ile Lys Glu Gly Ser Met Ser Glu Asp
            340                 345                 350

Glu Phe Ile Glu Glu Ala Lys Val Met Met Asn Leu Ser His Glu Lys
            355                 360                 365

Leu Val Gln Leu Tyr Gly Val Cys Thr Lys Gln Arg Pro Ile Phe Ile
            370                 375                 380

Ile Thr Glu Tyr Met Ala Asn Gly Cys Leu Leu Asn Tyr Leu Arg Glu
385                 390                 395                 400

Met Arg His Arg Phe Gln Thr Gln Gln Leu Leu Glu Met Cys Lys Asp
                405                 410                 415

Val Cys Glu Ala Met Glu Tyr Leu Glu Ser Lys Gln Phe Leu His Arg
            420                 425                 430

Asp Leu Ala Ala Arg Asn Cys Leu Val Asn Asp Gln Gly Val Val Lys
            435                 440                 445

Val Ser Asp Phe Gly Leu Ser Arg Tyr Val Leu Asp Asp Glu Tyr Thr
            450                 455                 460

Ser Ser Val Gly Ser Lys Phe Pro Val Arg Trp Ser Pro Pro Glu Val
465                 470                 475                 480

Leu Met Tyr Ser Lys Phe Ser Ser Lys Ser Asp Ile Trp Ala Phe Gly
                485                 490                 495

Val Leu Met Trp Glu Ile Tyr Ser Leu Gly Lys Met Pro Tyr Glu Arg
            500                 505                 510

Phe Thr Asn Ser Glu Thr Ala Glu His Ile Ala Gln Gly Leu Arg Leu
            515                 520                 525

Tyr Arg Pro His Leu Ala Ser Glu Lys Val Tyr Thr Ile Met Tyr Ser
            530                 535                 540

Cys Trp His Glu Lys Ala Asp Glu Arg Pro Thr Phe Lys Ile Leu Leu
545                 550                 555                 560

Ser Asn Ile Leu Asp Val Met Asp Glu Glu Ser
                565                 570

<210> SEQ ID NO 3
<211> LENGTH: 659
<212> TYPE: PRT
<213> ORGANISM: Homo sapiens

<400> SEQUENCE: 3

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
            35                  40                  45

Arg Gly Ser Lys Lys Gly Ser Ile Asp Val Glu Lys Ile Thr Cys Val
        50                  55                  60

Glu Thr Val Val Pro Glu Lys Asn Pro Pro Pro Glu Arg Gln Ile Pro
65                  70                  75                  80
```

```
Arg Arg Gly Glu Glu Ser Ser Glu Met Glu Gln Ile Ser Ile Ile Glu
                85                  90                  95
Arg Phe Pro Tyr Pro Phe Gln Val Val Tyr Asp Glu Gly Pro Leu Tyr
            100                 105                 110
Val Phe Ser Pro Thr Glu Glu Leu Arg Lys Arg Trp Ile His Gln Leu
        115                 120                 125
Lys Asn Val Ile Arg Tyr Asn Ser Asp Leu Val Gln Lys Tyr His Pro
    130                 135                 140
Cys Phe Trp Ile Asp Gly Gln Tyr Leu Cys Cys Ser Gln Thr Ala Lys
145                 150                 155                 160
Asn Ala Met Gly Cys Gln Ile Leu Glu Asn Arg Asn Gly Ser Leu Lys
                165                 170                 175
Pro Gly Ser Ser His Arg Lys Thr Lys Lys Pro Leu Pro Pro Thr Pro
            180                 185                 190
Glu Glu Asp Gln Ile Leu Lys Lys Pro Leu Pro Pro Glu Pro Ala Ala
        195                 200                 205
Ala Pro Val Ser Thr Ser Glu Leu Lys Lys Val Val Ala Leu Tyr Asp
    210                 215                 220
Tyr Met Pro Met Asn Ala Asn Asp Leu Gln Leu Arg Lys Gly Asp Glu
225                 230                 235                 240
Tyr Phe Ile Leu Glu Glu Ser Asn Leu Pro Trp Trp Arg Ala Arg Asp
                245                 250                 255
Lys Asn Gly Gln Glu Gly Tyr Ile Pro Ser Asn Tyr Val Thr Glu Ala
            260                 265                 270
Glu Asp Ser Ile Glu Met Tyr Glu Trp Tyr Ser Lys His Met Thr Arg
        275                 280                 285
Ser Gln Ala Glu Gln Leu Leu Lys Gln Glu Gly Lys Glu Gly Gly Phe
    290                 295                 300
Ile Val Arg Asp Ser Ser Lys Ala Gly Lys Tyr Thr Val Ser Val Phe
305                 310                 315                 320
Ala Lys Ser Thr Gly Asp Pro Gln Gly Val Ile Arg His Tyr Val Val
                325                 330                 335
Cys Ser Thr Pro Gln Ser Gln Tyr Tyr Leu Ala Glu Lys His Leu Phe
            340                 345                 350
Ser Thr Ile Pro Glu Leu Ile Asn Tyr His Gln His Asn Ser Ala Gly
        355                 360                 365
Leu Ile Ser Arg Leu Lys Tyr Pro Val Ser Gln Gln Asn Lys Asn Ala
    370                 375                 380
Pro Ser Thr Ala Gly Leu Gly Tyr Gly Ser Trp Glu Ile Asp Pro Lys
385                 390                 395                 400
Asp Leu Thr Phe Leu Lys Glu Leu Gly Thr Gly Gln Phe Gly Val Val
                405                 410                 415
Lys Tyr Gly Lys Trp Arg Gly Gln Tyr Asp Val Ala Ile Lys Met Ile
            420                 425                 430
Lys Glu Gly Ser Met Ser Glu Asp Glu Phe Ile Glu Glu Ala Lys Val
        435                 440                 445
Met Met Asn Leu Ser His Glu Lys Leu Val Gln Leu Tyr Gly Val Cys
    450                 455                 460
Thr Lys Gln Arg Pro Ile Phe Ile Ile Thr Glu Tyr Met Ala Asn Gly
465                 470                 475                 480
Cys Leu Leu Asn Tyr Leu Arg Glu Met Arg His Arg Phe Gln Thr Gln
                485                 490                 495
```

-continued

```
Gln Leu Leu Glu Met Cys Lys Asp Val Cys Glu Ala Met Glu Tyr Leu
            500                 505                 510
Glu Ser Lys Gln Phe Leu His Arg Asp Leu Ala Ala Arg Asn Cys Leu
        515                 520                 525
Val Asn Asp Gln Gly Val Val Lys Val Ser Asp Phe Gly Leu Ser Arg
        530                 535                 540
Tyr Val Leu Asp Asp Glu Tyr Thr Ser Ser Val Gly Ser Lys Phe Pro
545                 550                 555                 560
Val Arg Trp Ser Pro Pro Glu Val Leu Met Tyr Ser Lys Phe Ser Ser
                565                 570                 575
Lys Ser Asp Ile Trp Ala Phe Gly Val Leu Met Trp Glu Ile Tyr Ser
            580                 585                 590
Leu Gly Lys Met Pro Tyr Glu Arg Phe Thr Asn Ser Glu Thr Ala Glu
        595                 600                 605
His Ile Ala Gln Gly Leu Arg Leu Tyr Arg Pro His Leu Ala Ser Glu
    610                 615                 620
Lys Val Tyr Thr Ile Met Tyr Ser Cys Trp His Glu Lys Ala Asp Glu
625                 630                 635                 640
Arg Pro Thr Phe Lys Ile Leu Leu Ser Asn Ile Leu Asp Val Met Asp
                645                 650                 655
Glu Glu Ser

<210> SEQ ID NO 4
<211> LENGTH: 23
<212> TYPE: DNA
<213> ORGANISM: Homo sapiens

<400> SEQUENCE: 4
cccttgaacc tcctcgttcg acc                                       23

<210> SEQ ID NO 5
<211> LENGTH: 23
<212> TYPE: DNA
<213> ORGANISM: Homo sapiens

<400> SEQUENCE: 5
gagacgtgct acttccattt gtc                                       23

<210> SEQ ID NO 6
<211> LENGTH: 356
<212> TYPE: DNA
<213> ORGANISM: Homo sapiens

<400> SEQUENCE: 6
ttttggtgga ctctgctacg tagtggcgtt cagtgaaggg agcagtgttt tcccagatc    60 ctctggcctc cccgtccccg agggaagcca ggactagggt cgaatgaagg ggtcctccac   120
ctccacgttc cattcctgtt ccacctcaag gtcactggga acacctttcg cagcaaactg   180
ctaattcaat gaagacctgg agggagccaa ttgttccagt tcatctatca catggccagt   240
tggtccattc aacaaatggt tattggatgc ccattatgtg gcaggcactg ttccggggga   300
gagcacacag gtgaactcca gaaagaagaa gctatggccg cagtgattct ggagag       356
```

ISOFORM OF BRUTON'S TYROSINE KINASE (BTK) PROTEIN

CROSS REFERENCE TO RELATED APPLICATIONS

This application is a division of U.S. Ser. No. 12/531,061, filed Sep. 25, 2009, which is a national stage filing under 35 U.S.C. 371 of International Application PCT/EP2008/053099, filed on Mar. 14, 2008, which claims priority from Italian Application No. PD2007A000088, filed on Mar. 14, 2007, and EP Application No. 07106119.6, filed on Apr. 13, 2007. The entire content of each of the referenced Applications is incorporated herein by reference. International Application PCT/EP2008/053099 was published under PCT Article 21(2) in English.

DESCRIPTION

1. Technical Field

The present invention regards the use of compounds for the production of a medicament capable of modulating, and in particular diminishing the drug resistance in human epithelial tumour cells, according to the characteristics stated in the preamble of the main claim. It is also intended for a determination method of the drug resistance in tumour cells as well as a method for the identification of tumour stem cells.

2. Technological Background

One of the most commonly followed strategies in the therapy of neoplastic pathologies foresees the use of drugs (chemotherapy) capable of damaging the DNA of the tumour cells, so as to induce the natural process of apoptosis in the same.

Nevertheless, it is known that the tumour cells may respond in an unexpected manner to the drug therapy, showing, on the contrary, a strong resistance to the same. It is also known that one of the main reasons for the drug resistance shown by the tumour cells is the incapacity of the cells to begin the process of apoptosis, even in the presence of considerable DNA damage.

This phenomenon was traced back to a functional alteration (mutation or deletion) of the gene p53, which is no longer capable of initiating the process of cellular apoptosis, thus leading the cells to resist the drug action. The drug resistance levels of the tumour cells can be very high. For example, in the case of tumour cells of the colon-rectum in advanced phase, a drug therapy based on 5-fluorouracil (5FU) shows an effective response only for 10-15% of the cells, and a combination of 5FU with new drugs such as irinotecan and oxaliplatin leads to an increase of the cell mortality up to 40-50%, a value which is still entirely unsatisfactory for an effective therapeutic action towards the neoplastic pathologies.

In recent years, a cell phenomenon was discovered called "RNA interference" (RNAi) by means of which the gene expression is silenced in a specific manner. By taking advantage of such process, it is possible to obtain the selective silencing of genes with unknown function, thus permitting the definition of its specific function through the study of the obtained phenotype. By applying RNAi techniques and studying the phenotypic results, it is moreover possible to assign new functions to already known genes.

The genes involved in the phenomenon of drug resistance of the tumour cells are today largely unknown.

There is very much the need, therefore, to identify new genes involved in the drug-resistance and to design methods and compounds capable of substantially diminishing the tumour cells' resistance to drugs.

DESCRIPTION OF THE INVENTION

The problem underlying the present invention is that of making available compounds capable of reducing the drug resistance of the tumour cells of epithelial type, in order to permit the manufacture of medicaments destined for the therapy of related neoplastic pathologies.

This problem is resolved by the present finding by means of the use of compounds capable of functionally blocking one or more genes chosen from the group identified in the attached claims.

In a second aspect thereof, this invention moreover provides a method for the determination of the drug resistance of epithelial tumour cell lines.

In a further aspect thereof, this invention moreover provides a method for the identification of tumour stem cells.

BRIEF DESCRIPTION OF THE DRAWINGS

The characteristics and advantages of the invention will be clearer from the detailed description which follows of the tests and results which have led to its definition, reported with reference to the drawing set wherein.

IDENTIFICATION METHODOLOGY OF THE GENES MODULATING THE DRUG RESISTANCE IN EPITHELIAL TUMOUR CELLS AND RELATED VALIDATION TESTS

The abovementioned technical problem was tackled by subjecting several epithelial tumour cell lines to a series of tests and analyses geared to identify and characterise the genes capable of giving rise to the phenotypic expression of interest, i.e. the reversion of the resistance to the apoptosis induced by chemotherapeutic drugs.

Such identification was conducted by means of phenotypic screening of a representative cell line of the epithelial tumour cells following the selective silencing of an extended group of genes by means of RNAi.

This complex screening work was made possible due to a library of retroviral pRetroSuper (pRS) vectors recently made by the Bernards laboratories. It is known that such vectors are capable of expressing a specific oligonucleotide molecule in a stable manner, known as small interference RNA, in brief siRNA, capable of blocking the translation process of a specific messenger RNA (mRNA) in the corresponding protein. Such mechanism, in brief, foresees that the siRNA molecule (or rather a filament thereof) is associated with the RISC enzymatic complex, activating it, such that the latter can recognise and bind to the mRNA complementary to the siRNA associated thereto and then degrade it. It follows that the mRNA, identified in a specific manner by the siRNA, cannot be translated in the corresponding amino acid chain, thus obtaining the silencing of the gene from which the mRNA was transcribed. The interference process is specific, so that a siRNA molecule is normally capable of degrading only one mRNA and therefore silencing one single gene. On the other hand, it is instead possible that the same mRNA can be degraded, via RISC, by different siRNA.

This mechanism is one of the different possible modes for functionally blocking a gene (functional knockout). However, the consequent degradation of siRNA via RISC produces only a transient effect on protein levels, thus allowing only short term experiments whose results may be not relevant in the long term. To overcome this problem, short hairpin RNAs (shRNAs), a sequence of RNA folded in the shape of a hairpin, were used as a mechanism for functional knockout. In brief, a vector is used to introduce and incorporate shRNA into the cell chromosome. Transcription of the DNA produces shRNA which is subsequently cleaved by the cellular machinery, DICER, into siRNA. The siRNA then functions as previously mentioned. The incorporation of the shRNA vector into the cell chromosome allows for the gene silencing to be inherited by daughter cells. Thus the usage of shRNAs allows for functional knock out cells that can be used for long term experiments.

It is also known in the literature that the efficiency of transfection for siRNAs is never 100%. Therefore, the use of transfected siRNAs does not assure that all treated cells are successfully deprived of a target protein. The absence of a selectable marker further creates a problem in working with homogeneous populations of cells. Using a selectable marker, such as a puromycin resistance gene, along with a retroviral library, allows for recovery of only the cells bearing shRNAs. Moreover, following shRNA expression selection, only genes whose silencing is compatible with normal cell survival and proliferation are selected for. The absence of these genes does not influence normal cell physiology but only the response to anticancer drugs, a very important consideration while developing anticancer therapy.

It is nevertheless important to specify that the same effect can, in general, be reached by acting in any other step of a gene's protein coding process, such as for example the step of transcription of the gene in mRNA, or the step of mRNA transduction, or by means of inhibition of the protein resulting from the coding process.

It is evident that the essential and critical step in the resolution of the problem is represented by the identification of the responsible gene or genes of the desired phenotype.

The retroviral library arranged by the Bernards laboratories consists of about 25,000 different elements, capable of silencing about 8,300 genes of the human genome, with a ratio of about 3 different vectors for each gene.

The tests were initially conducted in vitro and subsequently validated ex vivo on different epithelial tumour cell lines, characterised by the lack of or by the mutation of the gene p53 and hence provided with a marked resistance to chemotherapeutic drugs.

In detail, a human RNAi library (NKi library) was established, consisting of 8,300 targeted genes for silencing. The targeted genes included kinases, phosphatases, oncogenes, tumor suppressors, transcription factors, genes involved in transformation, metastasis, cell cycle, differentiation, apoptosis, metabolic and anabolic processes. A protocol was followed similar to that mentioned in a prior publication (Berns et al., NATURE vol. 428, 25 Mar. 2004). The contents of this publication are incorporated by reference into this application. The mRNA sequence for each targeted gene was selected from UniGene. The sequences were masked using RepeatMasker to remove repetitive sequences and searched with NCBI BLAST against UniVec to mask for vector contamination. Three different 19 nucleotide (19-mer) sequences for silencing each targeted gene were designed, for a total of approximately 25,000 59-mer oligonucleotides that specify short hairpin RNAs (shRNAs). The 19-mer sequences were selected using a selection criteria as mentioned in the Berns publication wherein, a) there were no stretches of four or more consecutive T or A residues (to avoid premature polymerase III transcription termination signals); b) to have 30-70% overall GC content; c) to lie within the coding sequence of the target gene; d) to begin with a G or C residue (consistent with recently established rules for strand bias); e) to begin after an AA dimer in the 5' flanking sequence; f) to end just prior to a TT, TG or GT doublet in the 3' flanking sequence; g) to not contain XhoI or EcoRI restriction enzyme sites to facilitate subsequent shuttling of the knockdown cassette into vector backbones; h) to share minimal sequence identity with other genes; i) to target all transcript variants represented by RefSeq mRNAs; and j) to not overlap with other 19-mers selected from the same target sequence. The 59-mer oligonucleotides were designed as to contain a 19-mer sequence, its complimentary 19-mer sequence, pol III transcription initiation site, pol III termination site, and HindIII/Bg/II cloning sites. Utilizing the HindIII/Bg/II cloning sites, the oligonucleotides were ligated into pRetroSuper (pRS) retroviral vectors, which included a selection cassette for puromycin resistance. The DNA from the three different vectors that targeted the same gene was pooled and virus was produced to infect target cells.

Example 1

The tumour cell line initially used was HCT116p53KO (which differs from the wild type wt HCT116 due to the lack of gene p53), related to the colon tumour, while further detailed studies of specific genes were carried out on other drug-resistant tumour cell lines of the colon, such as DLD-1 and SW480, as well as on other tumour cell lines of the lung and ovary. In particular, all cell lines, object of the analysis, were related to tumours of epithelial type.

Preliminarily, cell lines HCT116p53KO, DLD-1 and SW480 were treated with common chemotherapeutic drugs in order to confirm their resistance to the drug-induced apoptosis.

The chemotherapeutic drugs usable in accordance with the present invention can be of any type suitable for inducing the apoptosis process in the affected tumour cells, such as for example an antimetabolite or any DNA-damaging agent comprising the inhibitors of the topoisomerase I, inhibitors of the topoisomerase II, the platinum coordination compounds and alkylating agents.

The aforesaid preliminary tests have shown how, after treatment for 72 hours in 200 µM 5FU, the cell mortality was less than 10%, against a wt HCR116 cell mortality of greater than 95%.

Supplementary tests of colony forming assays (CFA), have moreover demonstrated how such drug resistance was of non-transitory type. Once the resistance to apoptosis induced by chemotherapeutic drugs was confirmed, $200 \times 10^6$ HCT116p53KO cells were infected with the above-identified pRetroSuper library, provided by the Bernards laboratories. Each vector of this library was advantageously equipped with a selection cassette for a puromycin resistance gene, so that it was possible to select the HCT116p53KO cells actually infected by the vectors of the library through treatment with puromycin (2 mg/l in the culture medium for two days).

At the end of the antibiotic treatment, the still-living cells were then collected, which therefore comprised all of the cells infected by the retroviruses of the library whose silenced genes were not incompatible with the cellular survival.

The cells thus collected were then treated with 200 µM 5FU for 72 hours, while at the same time wt HCT116 cells and uninfected HCT116p53KO cells were also subjected to the same treatment, as controls.

At the end of the treatment, it was found that about half of the cells were floating in the culture medium, therefore dead. Such cells represented the sought-after phenotype, so that they were collected and subjected to the necessary treatment for the identification of the genes silenced by the retroviral library.

In brief, such treatments comprised of the extraction of the DNA and the amplification by means of PCR (Polymerase Chain Reaction) of a region of 643 base pairs containing the region H1 of a specific promoter and the adjacent region coding the nucleotide sequence of interest. PCR amplification was performed using a pRS-fw primer: 5'-CCCT-TGAACCTCCTCGTTCGACC-3' (SEQ ID NO: 4) and pRS-rev primer: 5'-GAGACGTGCTACTTCCATTTGTC-3' (SEQ ID NO: 5). The products obtained by the amplification were then bound in pRS retroviral vectors and the infection process of HCT115p53KO cells was completely repeated with the new vectors, so as to refine the screening. The products were digested with EcoRI/XhoI and recloned into pRS.

The products obtained from the second amplification treatment with PCR on the DNA harvested from the dead cells after new treatment with 5FU were newly isolated and bound in retroviral vectors pRS and then used for transforming DH5alpha bacteria whose respective plasmids were sequenced for the identification of the genes which gave rise to the phenotypic expression of interest.

Once the single genes were obtained and identified whose silencing by means of interference with RNA gave rise to the reversion of the resistance of the tumour cells tested to the 5FU, the separated and independent validation of the single genes took place.

Firstly, the validation was carried out in vitro on HCT116p53KO tumour cell samples, each of which separately infected with one of the previously-made plasmids, so as to silence in a specific and stable manner one of the genes indicated by the preceding screening and verify its capacity to modulate the resistance to drugs. The samples were then selected with puromycin, placed in Petri dishes at 50% confluence and treated with 200 µM of 5FU for 12 hours.

The evaluation of the reversion of the drug resistance was carried out by means of observation of the formation of colonies according to the protocol defined by the CFA and their comparison with a wt HCT116 sample and an uninfected HCT116p53KO sample.

Figures 1, 2A, 2B:
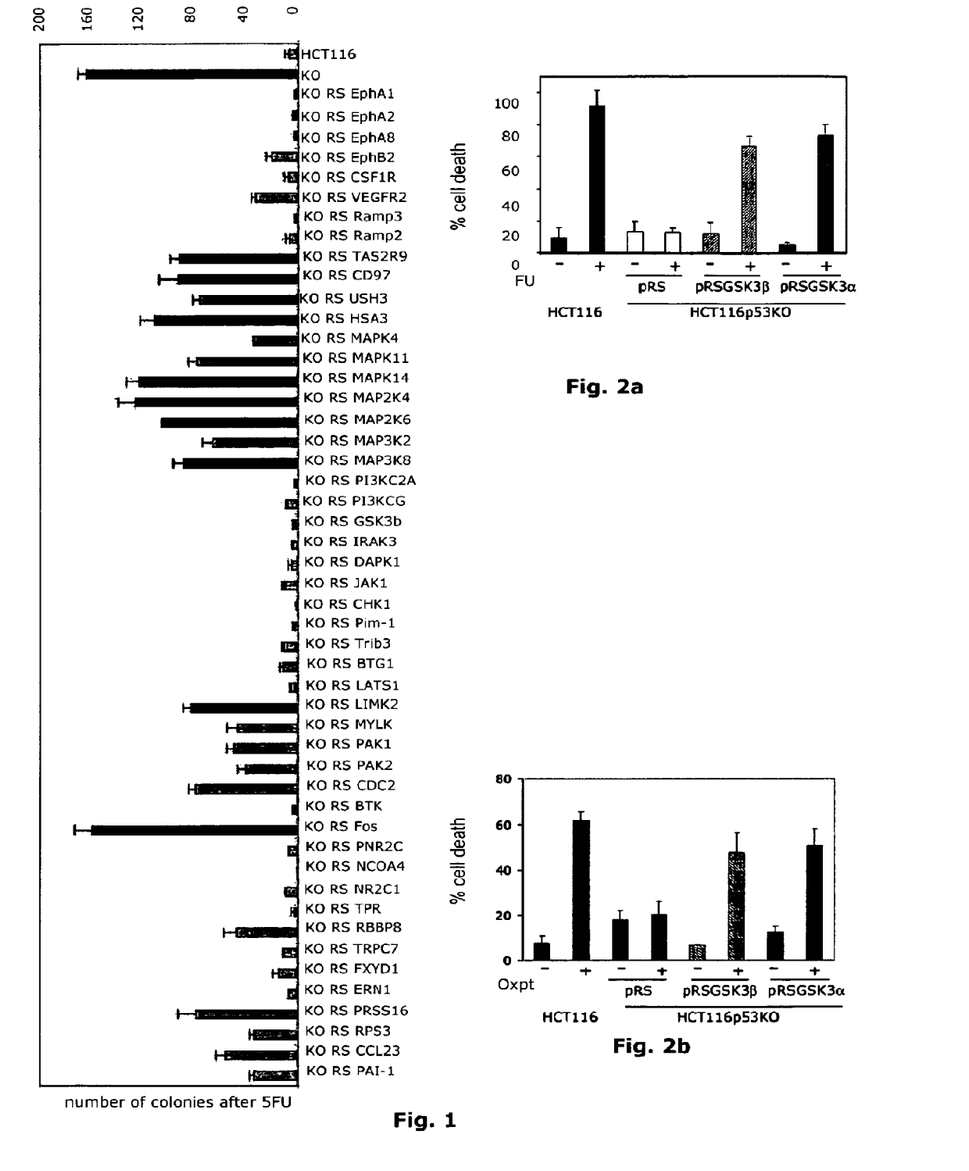
FIG. 1 is a graph illustrating the results of inhibition of the capacity to form drug-resistant tumour cell colonies of the colon treated with the compounds according to the invention and a chemotherapeutic drug.
FIGS. 2a and 2b are graphs showing the results of an analysis of reversion of the resistance of a tumour cell line to two different chemotherapeutic drugs by means of silencing of the alpha and beta isoforms of the gene GSK3.

In FIG. 1, the results are reported in graph form which were obtained from this first in vitro validation. As clearly shown by the graph, a high percentage of identified genes are capable, when functionally blocked, of consistently reverting the colony forming ability of 5FU-treated HCT116p53KO cells. HCT116 and KO represent positive and negative controls.

This first validation has in particular permitted identifying a group of genes whose specific silencing has given rise to a 5FU-induced inhibition of the growth of the tumour colonies greater than 50% with respect to the HCT116p53KO sample.

These genes, themselves known and characterised, are listed below with their official symbol together with their identification number (between parentheses) reported on the NCBI Entrez Gene data bank: EphA1 (2041), EphA2 (1969), EphA8 (2046), EphB2 (2048), CSF1R (1436), VEGFR2 (3791), RAMP2 (10266), RAMP3 (10268), CLRN1 (7401), MAPK4 (5596), PIK3C2A (5286), PIK3CG (5294), GSK3beta (2932), IRAK3 (11213), DAPK1 (1612), JAK1 (3716), CHEK1 (1111), PIM1 (5292), TRB3 (57761), BTG1 (694), LATS1 (9113), LIMK2 (3985), MYLK (4638), PAK1 (5058), PAK2 (5062), CDC2 (983), BTK (695), PNRC2 (55629), NCOA4 (8031), NR2C1 (7181), TPR (7185), RBBP8 (5932), TRPC7 (57113), FXYD1 (5348), ERN1 (2081), PRSS16 (10279), RPS3 (6188), CCL23 (6368) and SERPINE1 (5054).

Among the above-listed genes, a first subgroup is also identifiable of genes whose silencing advantageously leads to an over 75% inhibition of the tumour cells growth.

Such first subgroup is formed by the following genes:

EphA1 (2041), EphA2 (1969), EphA8 (2046), EphB2 (2048), CSF1R (1436), VEGFR2 (3791), RAMP2 (10266), RAMP3 (10268), MAPK4 (5596), PIK3C2A (5286), PIK3CG (5294), GSK3beta (2932), IRAK3 (11213), DAPK1 (1612), JAK1 (3716), CHEK1 (1111), PIM1 (5292), TRB3 (57761), BTG1 (694), LATS1 (9113), LIMK2 (3985), BTK (695), PNRC2 (55629), NCOA4 (8031), NR2C1 (7181), TPR (7185), TRPC7 (57113), FXYD1 (5348), ERN1 (2081), RPS3 (6188) and SERPINE1 (5054).

In a more advantageous manner, a second subgroup was further identified of genes whose silencing advantageously leads to an over 95% inhibition of the growth of the tumour cells.

Such subgroup is formed by the following genes:

EphA1 (2041), EphA2 (1969), EphA8 (2046), RAMPS (10268), PIK3C2A (5286), GSK3beta (2932), IRAK3 (11213), DAPK1 (1612), CHEK1 (1111), PIM1 (5292), BTK (695), NCOA4 (8031), TPR (7185).

The gene GSKalpha (2931), isoform of the gene GSK3beta, must be added to the above-listed genes; in separate tests whose results are shown by the graphs of FIGS. 2a and 2b it has shown an optimal efficiency in the reversion of the resistance both to 5FU and to the oxaliplatin in HCT116p53KO cells, entirely comparable to its beta isoform. In detail, FIG. 2a compares the percentages of cell deaths in the absence (symbol "−") and presence (symbol "+") of 200 µM 5FU (72 hr treatment) upon wild type (wt) HCT116 cells, HCT116p53KO drug resistant cells, GSK3alpha and GSK3beta silenced gene cells. In comparison to the HCT116p53KO drug resistant cells, HCT116p53KO cells with GSK3alpha and GSK3beta genes silenced resulted in a high percentage of tumour cell death in the presence of 5FU. FIG. 2b compares the percentages of cell deaths in the absence (symbol "−") and presence (symbol "+") of 50 µM oxaliplatin (72 hr treatment) upon wt HCT116 cells, HCT116p53KO drug resistant cells, GSK3alpha and GSK3beta silenced gene cells. In comparison to the HCT116p53KO drug resistant cells, HCT116p53KO cells with GSK3alpha and GSK3beta genes silenced also resulted in a high percentage of tumour cell death in the presence of oxaliplatin.

The formal confirmation of the silencing of the specific genes by means of interference was carried out through Western Blot analysis of the levels of the protein coded by them, if the antibody was commercially available (EphA1, EphA2, CSF1R, VEGFR, GSK3, JAK1, CHEK1, LIMK2, CDC2, BTK). Western Blot analysis was performed by lysing the puromycin-selected cells in E1A buffer (50 mM Hepes pH 8; 500 mM NaCl; 0.1% NP 40; DTT 1M; EDTA 1 mM). 8-12% SDS-polyacrylamide gel electrophoresis was used to separate 30 µg of protein, which was later transferred to polyvinylidine difluoride membranes. Antibodies were then used to probe the Western Blots.

The effectiveness of the plasmids capable of silencing the genes belonging to the above-identified group was further tested on DLD-1 and SW480, other tumour cell lines of the colon known for possessing mutated p53 and for their resistance to drugs.

The capacity to diminish the resistance to chemotherapeutic drugs was generally confirmed, even with different performances. In particular, the inhibition percentage of the growth of colonies after drug treatment over all three cell lines was optimal when the following genes were silenced:

EphA1 (2041), EphA2 (1969), EphA8 (2046), EphB2 (2048), CSF1R (1436), VEGFR2 (3791), PIK3C2A (5286), PIK3CG (5294), GSK3alpha (2931), GSK3beta (2932), IRAK3 (11213), CDC2 (983), CHEK1 (1111), LATS1 (9113), TRB3 (57761), JAK1 (3716), BTK (695), PIM1 (5292), LIMK2 (3985), PAK2 (5062).

Example 2

Figure 3A:
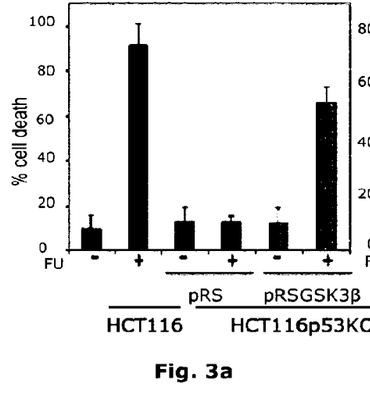
FIGS. 3a-3c are graphs illustrating the results of the tests of reversion of the resistance to a chemotherapeutic drug of three different tumour cell lines of the colon by means of silencing of the gene GSK3beta.
Figures 3B, 3C:
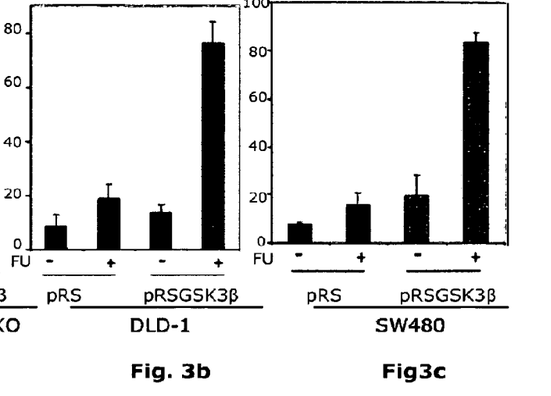

As an example, in FIGS. 3a-3c graphs are reported following silencing tests of the gene GSK3beta in the three tested tumour cell lines, in which the fraction of dead cells after the treatment with 5FU in samples infected with vectors capable of silencing the aforesaid gene is reported and compared with samples infected with empty vectors. In detail, FIG. 3a compares the percentages of cell deaths in the absence (symbol "−") and presence (symbol "+") of 200 µM 5FU (72 hr treatment) upon wt HCT116 cells, HCT116p53KO drug resistant cells, and GSK3beta silenced gene cells. In comparison to the HCT116p53KO drug resistant cells, HCT116p53KO cells with GSK3beta gene silenced resulted in a high percentage of tumour cell death in the presence of 5FU. FIG. 3b compares the percentages of cell deaths in the absence (symbol "−") and presence (symbol "+") of 200 µM 5FU (72 hr treatment) upon wt DLD-1 cells and GSK3beta silenced gene DLD-1 cells. In comparison to the wt DLD-1 cells, GSK3beta silenced gene DLD-1 cells resulted in a high percentage of tumour cell death in the presence of 5FU. FIG. 3c compares the percentages of cell deaths in the absence (symbol "−") and presence (symbol "+") of 200 µM 5FU (72 hr treatment) upon wt SW480 cells and GSK3beta silenced gene SW480 cells. In comparison to the wt SW480 cells, GSK3beta silenced gene SW480 cells resulted in a high percentage of tumour cell death in the presence of 5FU.

In addition to 5FU, representative example of the family of chemotherapeutic drugs of the antimetabolic type, the reversion of the resistance to drugs was also tested on chemotherapeutic drugs of different types, such as oxaliplatin.

Figure 4A:
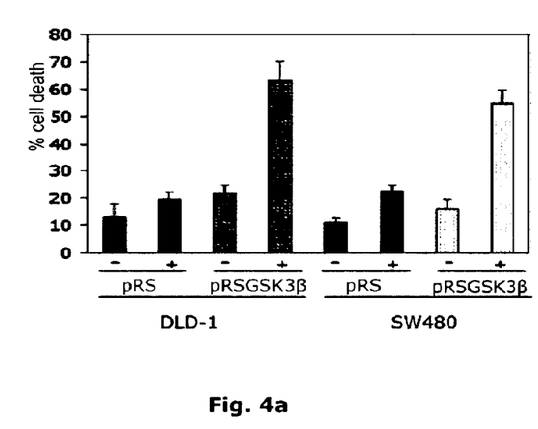
FIG. 4a is a graph illustrating the results of the tests of reversion of the resistance to a different chemotherapeutic drug of two different tumour cell lines of the colon by means of silencing of the gene GSK3beta.

In FIG. 4a, the fractions of dead cells induced by a treatment with oxaliplatin (50 µM) are reported in samples of colon tumour cell lines DLD-1 and SW480, respectively infected with empty vectors and with vectors silencing the gene GSK3beta.

Figure 4B:
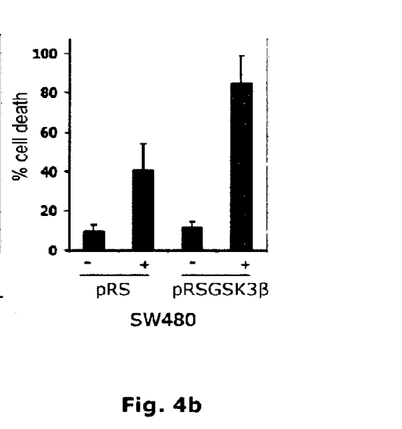
FIG. 4b is a graph illustrating the results of an analysis of reversion of the resistance of a tumour cell line to the combination of two different chemotherapeutic drugs by means of the silencing of the beta isoform of the gene GSK3.

The substantial diminution of the resistance to the apoptosis induced by oxaliplatin in the sample in which GSK3beta was silenced is evident. In FIG. 4b, a graph is reported in which the results of an analogous test are indicated on the cell line SW480, in which the drug used was a combination of 5FU and oxaliplatin.

As mentioned previously and shown in FIGS. 2a and 2b, GSK3alpha silencing has the same effect as GSK3beta in modulating the apoptotic response to 5FU and oxaliplatin.

Figure 5:
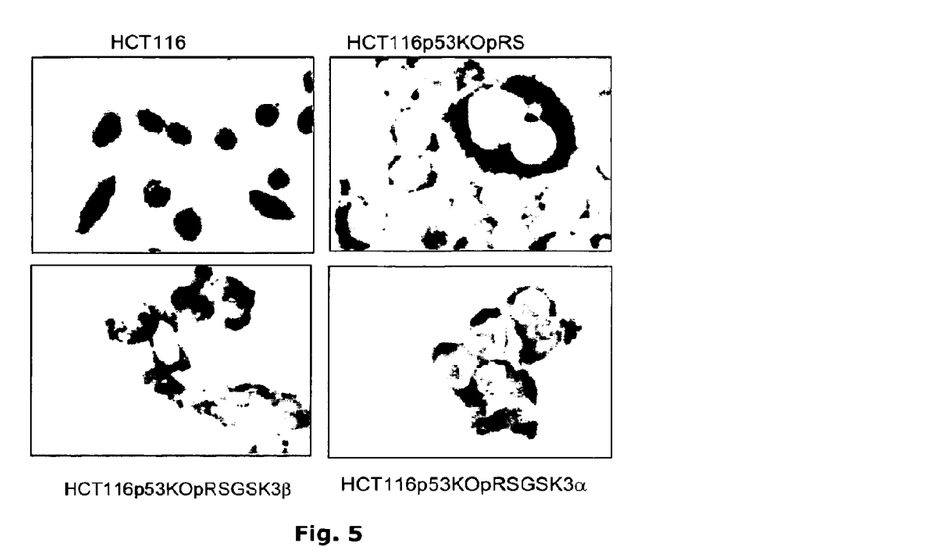
FIG. 5 is a collection of images illustrating the location of cytochrome C for 5FU-induced cell death in the absence of GSK3.
Figure 6:
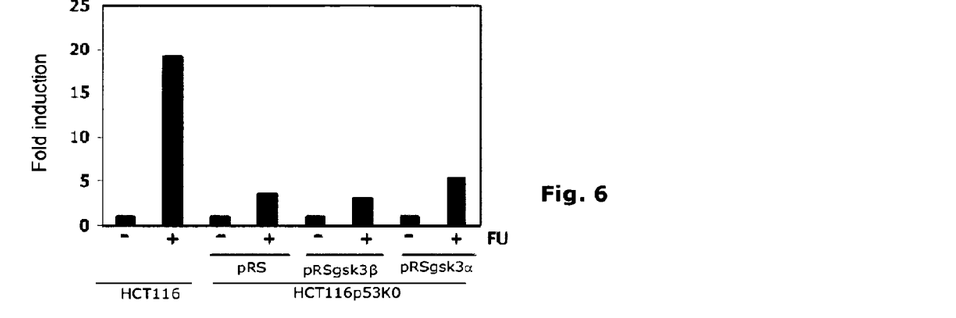
FIG. 6 is a graph illustrating the results of caspase 3 and caspase 7 activation assays in response to 5FU treatment of HCT116 and GSK3alpha, GSK3beta gene silenced HCT116p53KO colon carcinoma cells.
Figure 7:
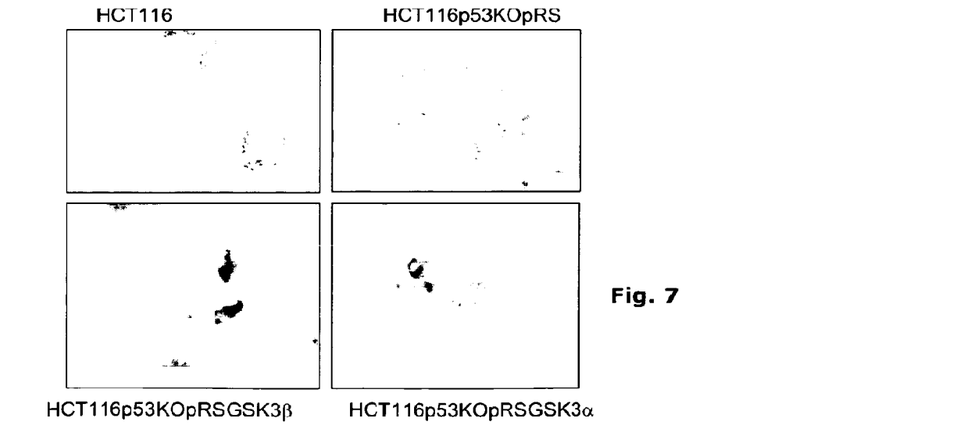
FIG. 7 is a collection of images illustrating the translocation of AIF to the nucleus during 5FU-induced cell death in the absence of GSK3.

Further study was conducted to determine if 5FU-induced cell death in the absence of GSK3 was cytochrome C-dependent or independent. Utilizing anti-cytochrome C and DAPI staining, as shown in FIG. 5, it was found that 5FU-induced cell death in the absence of GSK3 is cytochrome C-independent. More specifically, utilizing anti-AIF and DAPI staining, as shown in FIG. 7, it was discovered that in the absence of GSK3, AIF translocates to the nucleus resulting in cell death. This was further supported by the finding that caspases 3 and 7 were not activated during 5FU-induced cell death in GSK3 silenced cells, as shown in FIG. 6.

Example 3

Another particularly representative example of the above-identified gene group is constituted by the gene BTK, on which several investigations were undertaken.

BTK kinase is a cytoplasmic protein tyrosine kinase crucial for B-cell development and differentiation. BTK mutation is in fact responsible for X-linked agammaglobulinemia (XLA), a primary immunodeficiency mainly characterized by lack of mature B cells as well as low levels of immunoglobulins. In B cells BTK has been reported as having either pro-apoptotic or anti-apoptotic functions. Moreover, BTK has been so far assumed as being expressed only in some bone marrow-derived lineages such as B and mast cells, erythroid progenitors, platelets. Our finding that 18 BTK is a gene whose silencing reverts resistance to the cytotoxic action of 5FU demonstrated for the first time that BTK is expressed also in cell types others than cells of the hematopoietic lineage. Firstly, the effectiveness was tested of the reversion of the resistance to drugs in HCT116p53KO tumour cells treated with an inhibitor compound of the protein BTK, such to demonstrate how the functional blocking of the gene of interest can be carried out in alternative ways to the silencing by means of RNAi.

The compound employed in these tests was (2Z)-2-cyan-N-(2,5-dibromophenyl)-3-hydroxy-2-butenamide, known as LFM-A13, whose structural formula is reported below in Formula I.

Formula 1

Figure 8:
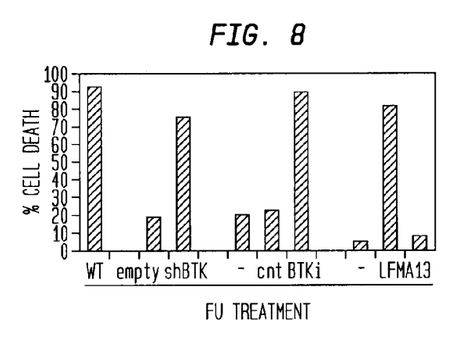
FIG. 8 is a graph illustrating the reversion of the resistance to a chemotherapeutic drug of a tumour cell line carried out by means of functional blocking of the gene BTK obtained with different methods.

In FIG. 8, the results of the comparison test are reported in a graph of the functional blocking of the BTK gene by means of plasmids, siRNA or LFM-A13 in samples of HCT116p53KO cells treated with 5FU. It can be easily noted how the obtained level of reversion to the drug resistance, expressed by means of the percentage fraction of dead cells, is entirely comparable. In detail, FIG. 8 compares the percentages of cell deaths in the presence of 200 μM 5FU (72 hr treatment) upon wt HCT116 cells and HCT116p53KO drug 19 resistant cells with or without (symbol "empty" and "–") specific depletions of BTK following transient siRNA transfection (symbol "BTKi"), stable retroviral-mediated RNA interference (symbol "shBTK"), and using LFMA13, an inhibitor compound of BTK.

Figure 9:
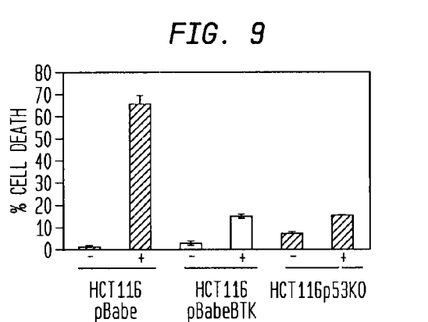
FIG. 9 is a graph illustrating the percentage of cell death induced by 5FU upon BTK overexpression in HCT116 colon carcinoma cells.

According to the protective effect of BTK revealed by the above described inhibition experiments, BTK overexpression protects sensitive HCT116 wt from 5FU-induced cell death. In detail, FIG. 9 compares the percentages of cell deaths in the presence of 200 μM 5FU (72 hr treatment) upon wt HCT116 cells infected with empty pBabe vector, wt HCT116 cells infected with pBabe BTK vector and HCT116p53KO drug resistant cells.

Figure 10A:
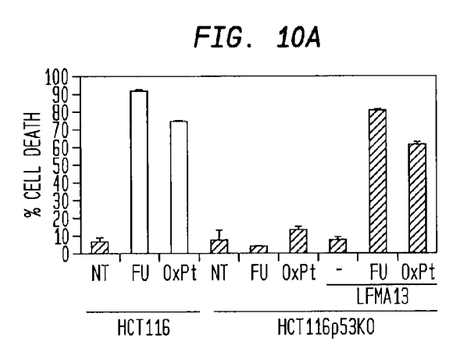
FIGS. 10a and 10b are graphs illustrating the reversion of the resistance to chemotherapeutic drugs by means of the functional blocking of the gene BTK on different colon tumour cell lines.
Figure 10B:
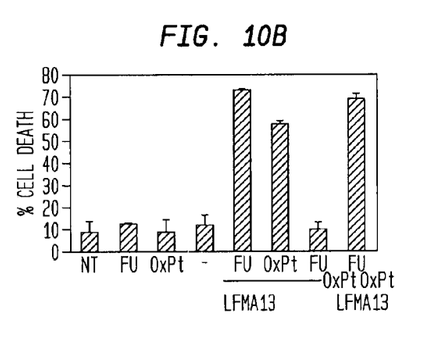

It was also determined that BTK inhibition reverts resistance also to oxaliplatin (FIG. 10a) and in DLD-1 (FIG. 10b).

Figure 11:
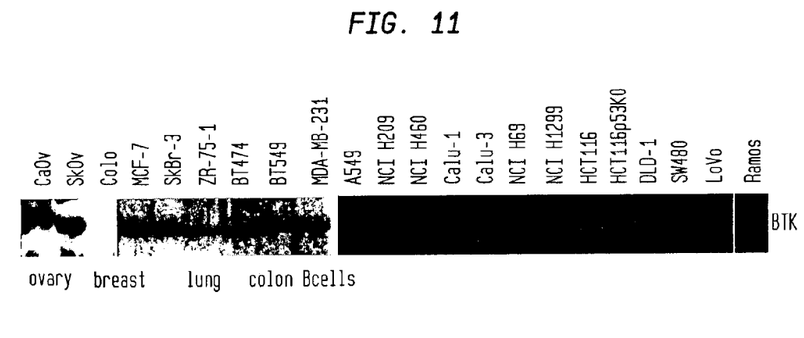
FIG. 11 is a western blot analysis showing BTK expression in several tumoral cell lines derived from different epithelial cancers.

The diminution of the resistance to chemotherapeutic drugs following the functional blocking of the gene BTK by means of LFM-A13 was further confirmed by tests conduct in vitro on epithelial tumour cell lines different from those of the colon. In FIG. 11 levels of BTK have been investigated, by means of Western blot, in several different epithelial carcinoma cell lines showing that the kinase is expressed in most of them. In particular, in FIGS. 12a and 12b, graphs were reported of the reversion tests obtained on SKOV cell lines (related to an ovarian tumour) and A549 cell lines (related to a lung tumour).

Figure 12A:
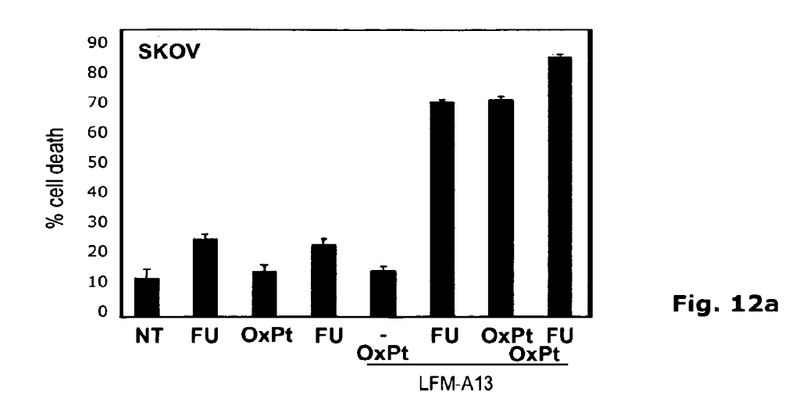
FIGS. 12a and 12b are graphs illustrating the reversion of the resistance to chemotherapeutic drugs by means of the functional blocking of the gene BTK on epithelial tumour cell lines other than colon.
Figure 12B:
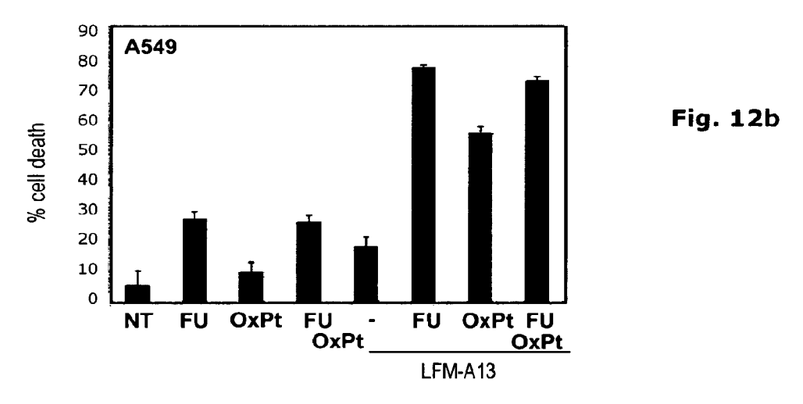

In detail, FIG. 12a compares the percentages of cell deaths in the absence (symbol "NT" and "–") and presence of 200 μM 5FU, 50 μM OxPt, and the combination of the two upon resistant ovarian (SKOV) cells with or without BTK inhibition through the usage of LMFA13. In comparison to the SKOV cells without LMFA13, the SKOV cells with LMFA13 resulted in a high percentage of tumour cell death. FIG. 12b compares the percentages of cell deaths in the absence (symbol "NT" and "–") and presence of 200 μM 5FU, 50 μM OxPt, and the combination of the two upon resistant lung (A549) cells with or without BTK inhibition through the usage of LMFA13. In comparison to the A549 cells without LMFA13, the A549 cells with LMFA13 resulted in a high percentage of tumour cell death.

In both cases, it is noted how the treatment of the cell lines with LFM-A13, functional inhibitor of the BTK gene, leads to a considerable increase of the cellular mortality after exposure to 5FU or oxaliplatin or both drugs in combination.

Moreover, the high effectiveness of the action of diminution of the drug-resistance also in these cell lines, confirms that the validity of the results obtained in the preceding tests can be extended at least to all types of epithelial tumour, such as lung tumour, ovarian tumour and breast tumour.

The optimal results pointed out above have suggested validating the gene BTK also through ex-vivo analysis on epithelial human tumour samples.

Firstly, it was verified through Western Blot that the BTK protein levels were high in 30% of the samples of ovarian tumour cells drawn from patients in advanced stage of disease and/or resistant to chemotherapeutic drugs.

Secondly, examinations were conducted on colon tumour stem cells isolated from patients in order to verify if the investigated genes were expressed (and in what measure) also in this cell type. In fact, according to recent studies (Dean et al., 2005), these stem cells would be the responsible principals of the drug resistance.

In all four tumour stem cell lines analysed, isolated from different patients, the expression of the protein BTK is very high, at least 4-5 times greater than the expression detected on the colon carcinoma cell lines used in the functional experiments, suggesting that the determination of the BTK levels can advantageously be used as a method for defining the stem cell properties of the tumour cells examined, and consequently also their resistance to chemotherapeutic drugs.

Figure 13:
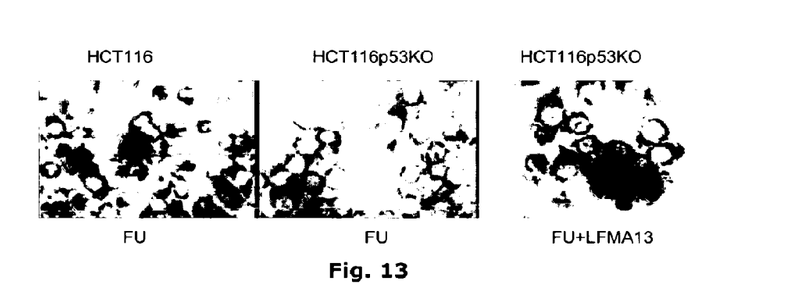
FIG. 13 is collection of images illustrating the cytoplasmic accumulation of cytochrome C in 5FU-treated cells upon BTK inhibition.
Figure 14:
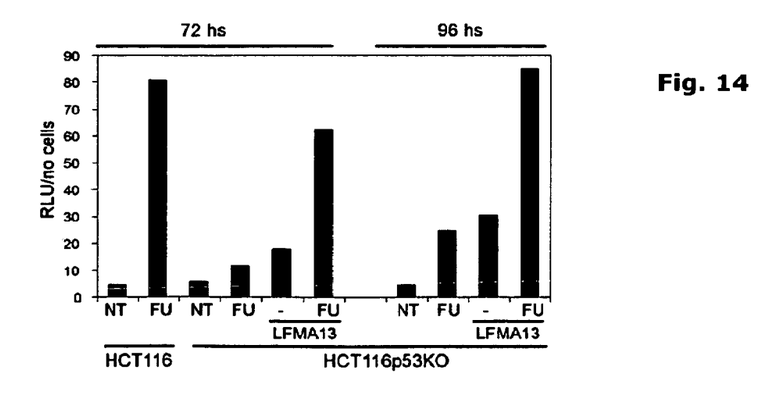
FIG. 14 is a graph illustrating the results of fluorimetric caspase activation assays after 72 hrs and 96 hrs in HCT116 and HCT116p53KO colon carcinoma cells treated with 5FU, BTK inhibition, or the combination of the two.

The results have shown that BTK levels determine the sensitivity of tumor cells to 5FU and that BTK inhibition reverses drug-resistance. Anti-cytochrome C immunostaining in 5FU-treated cells (FIG. 13) showed cytoplasmic accumulation after 5FU treatment in resistant cells only when BTK was inhibited, supporting the finding that reversal of drug-resistance upon BTK inhibition is due to activation of apoptosis. The same finding is also supported by the graph reported in FIG. 14, evaluating the level of caspase 3/7 activation upon 5FU treatment in HCT116p53KO resistant cells in the presence or in the absence of BTK inhibitor LFM-A13. High levels of caspase 3/7 activation, measured by means of a luminometric assay as RLU/number of cells, are observed in 5FU-treated HCT116p53KO cells only when BTK is inhibited.

Figure 15A:
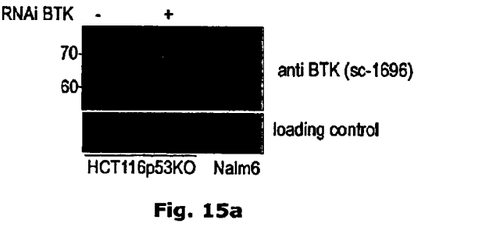
FIG. 15a is western blot image showing that antibody sc-1696 specifically recognizes BTK protein and that in epithelial carcinoma cells (HCT116p53KO) BTK has an apparent molecular weight of ~67 kDa and that the same form of the protein is present, together with the "classic" 77 kDa form, also in leukemic cells (Nalm6)

The predicted and reported molecular weight of BTK protein is 77 kDa. The protein identified in western blot as BTK by a specific antibody (sc-1696, from Santa Cruz Biotechnology) in HCT116p53KO and in all other epithelial carcinoma cell lines tested (6 breast cell lines, 3 ovary cell lines, 7 lung cell lines, 5 colon cell lines), in contrast, has an apparent molecular weight around 65-68 kDa (FIG. 11, FIG. 15a) suggesting that in epithelial cell 22 lines a shorter BTK isoform is expressed.

Figure 15B:
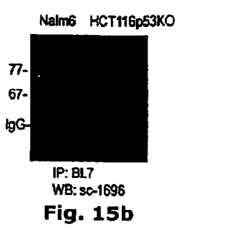
FIG. 15b is an immunoprecipitation-western blot image confirming that also a different antibody (BL7) identify BTK protein as being ~67 kDa in HCT116p53KO cells and that this isoform is present in leukemic cells (Nalm6) together with the "classic" 77 kDa form.

To confirm these results an immunoprecipitation analysis was carried out using two different and specific BTK antibodies (the above cited sc-1696 and BL7, kind gift of Dr. Mike Tomlinson, University of Birmingham, UK). The results in FIG. 15b show that only this novel isoform is expressed in epithelial cell lines whereas in a leukemic cell line (Nalm6), already known from the literature to express the classical 77 kDa form, both isoforms are present.

Therefore, a bioinformatic analysis of BTK coding sequence (cds) has been carried out and, accordingly, a second nucleotide triplet ATG (nt 428-430), in frame with the one known to be used to translate BTK (nt 164-166) and susceptible to start the translation of a protein has been identified. The expected molecular weight of the putative protein translated starting from this second ATG is 67 kDa, consistent with the apparent molecular weight of the band identified by different BTK antibodies in epithelial carcinoma cells.

Figure 16:
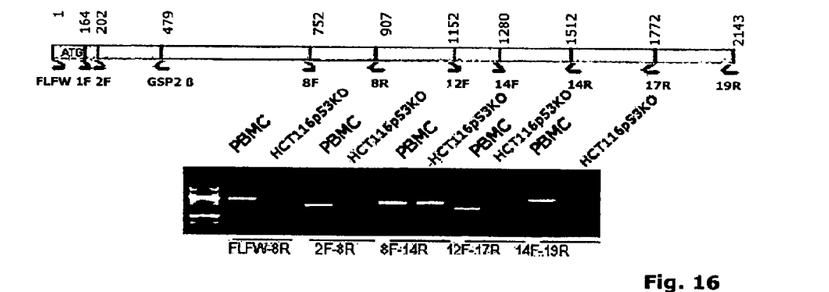
FIG. 16 is an image illustrating the results of a PCR experiment showing that the 5' end upstream of nucleotide 202 in the BTK-encoding mRNA from HCT116p53KO cells is absent or different from the 5' end of BTK mRNA from peripheral blood mononuclear cells (PBMC)

In order to identify which portion is missing in the mRNA coding for the shorter and novel isoform of the BTK protein, PCR experiments using different primers pairs (annealing at different parts of the cds as indicated in the upper diagram of FIG. 16) have been performed. As shown in FIG. 16, these experiments indicate that the 5' end, upstream of nucleotide 202, is absent or different in HCT116p53KO cells.

Figure 17:
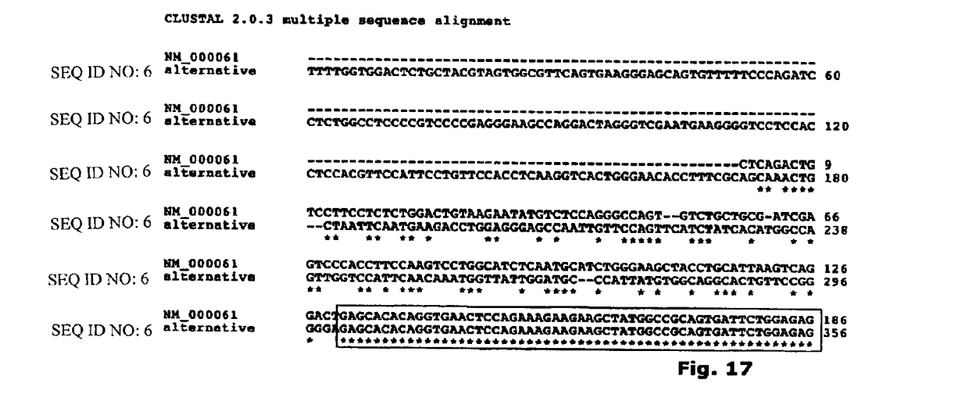
FIG. 17 is an image illustrating the results of ClustalW alignment of BTK transcript, identified by GenBank Accession #NM_000061, and the novel transcript identified in HCT116p53KO cells by 5'RACE PCR followed by cloning and sequencing (indicated as alternative), the box outlining the part of BTK sequence (starting from nucleotide 131 of the known transcript) common between BTK mRNA deriving from #NM_000061 and the novel BTK transcript found in HCT116p53KO.

5'RACE/sequencing experiments have been performed on mRNA from HCT116p53KO cells in order to determine the identity of the unknown 5' end. Subsequently, alignment analysis between the cDNA derived from mRNA from HCT116p53KO cells and the cDNA deriving from the standard BTK mRNA, identified by GenBank accession #NM_000061, using ClustalW computer program (results shown in FIG. 17) demonstrated that the sequence upstream of the second exon (starting at nt 134 of the cds) is different from what reported in literature, i.e., epithelial colon carcinoma cells express a different first exon.

Figure 18:
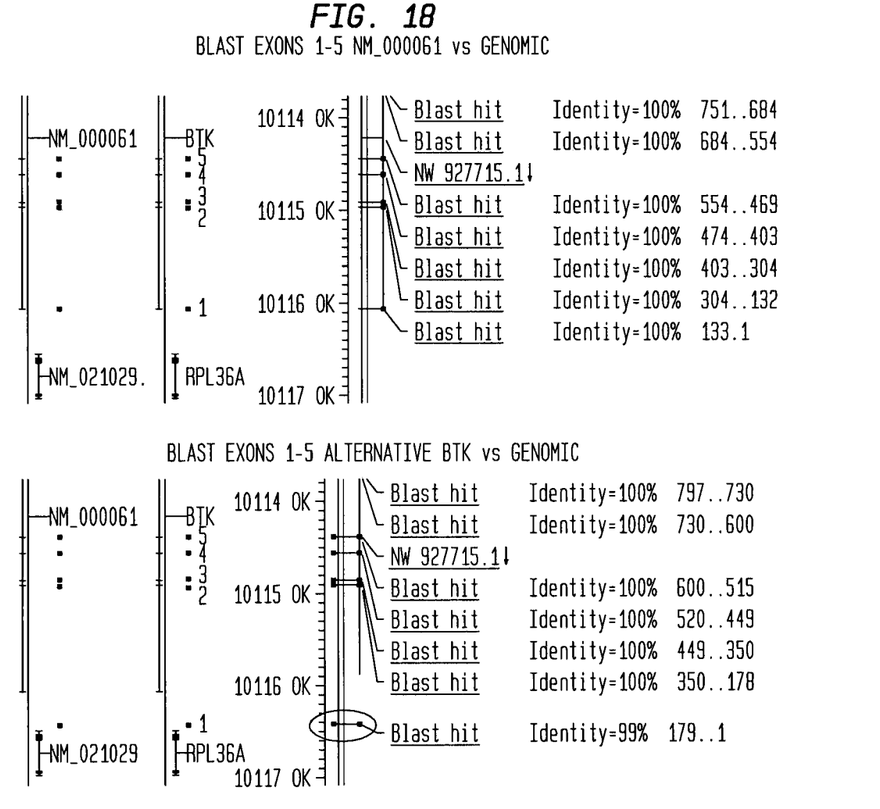
FIG. 18 is an image illustrating the results of a Blast alignment vs a genomic database of exons 1-5 of BTK transcript identified by GenBank Accession # NM_000061 and the same exons of the novel BTK transcript, the dots indicating the position on chromosome X of the different exons of BTK.

BLAST analysis using a genomic database (FIG. 18) localize the first exon of NM_000061 BTK transcript at 101160K on the chromosome X contig, in correspondence with the beginning of BTK locus. At variance, the first exon of the novel BTK transcript alignes 15192 by 5' of the first known BTK exon, immediately downstream of the RPL36A locus, suggesting that it corresponds to a hitherto unrecognized BTK exon. Moreover, this novel exon is present in HCT116p53KO instead of the first "classical" exon suggesting that this is an "alternative" first exon, whose usage gives raise to a different BTK mRNA, transcribed in cells expressing this shorter BTK isoform.

Figure 19:
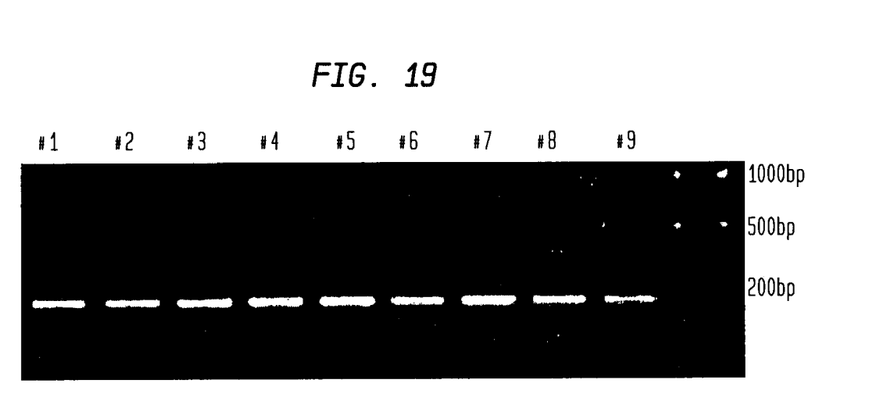
FIG. 19 is an image illustrating the results of a nested PCR experiment showing that the novel BTK transcript is expressed in Formalin-Fixed Paraffin-Embedded (FFPE) tumoral tissues from coloncarcinoma patients.

PCR/sequencing experiments demonstrated the expression of this "alternative" BTK mRNA not only in all colon-carcinoma cell lines tested (HCT116p53KO, DLD-1 and SW480) but also in 9/9 FFPE-samples from colon carcinoma patients (FIG. 19).

It should be noted that the first exon of BTK, as identified by GenBank accession # NM_000061, corresponds to the 5'UTR of the mRNA, being the ATG triplet encoding the first Met amino acid of BTK protein located in the second exon. 5'UTRs usually perform regulatory functions such as directing cap-dependent or IRES-mediated cap-independent translation. A different first exon, as identified in the novel transcript, can therefore dictate whether a different ATG (in this case an ATG located in the 4th exon) has to be used to start the translation of BTK protein, and therefore regulate the expression of different isoforms.

The nucleotide sequence of the first exon corresponding to the 5'UTR of the novel mRNA expressed by the BTK gene is reported in SEQ ID NO:1, attached to the present description.

The amino acid sequence of the novel isoform of BTK protein coded by the novel transcript is reported in SEQ ID NO:2, attached to the present description.

The above results suggest a method for determining the resistance of tumour cells to chemotherapeutic drugs as well as a method for the identification of the presence of tumour stem cells, wherein the expression of gene BTK comprises the steps of verifying the presence of the novel isoform of the BTK protein.

The presence of the novel isoform of the BTK protein may be controlled verifying the presence of the protein, for instance using western blot or immunoprecipitation or immunochemistry or immunofluorescence analysis, or, preferably, verifying the presence of the mRNA having the alternative first exon, whose cDNA shows the nucleotide sequence defined in SEQ ID NO:1. The latter may be advantageously carried out by means of PCR analysis, preferably using primers having a sequence included in SEQ ID NO:1.

This new method is expected to show relevant advantages, whit respect to the known prior art, particularly when used for analysing tumoral tissues taken from human patients.

Actually, it is well known that tumoral tissues taken from human patients may contain an effective amount of lymphocytes which may also express BTK protein, thus disturbing the search of BTK protein expressed by the tumoral cells.

However, BTK protein expressed by lymphocytes is the "classical" isoform of BTK protein having a molecular weight of 77 KDa, so that the search of the novel isoform of BTK protein may be carried out without any interference, with a simple PCR analysis looking for the presence of BTK mRNA having the alternative first exon.

The present invention therefore resolves the above-lamented problem with reference to the mentioned prior art, offering at the same time numerous other advantages, including making possible the development of diagnostic methods capable of predicting the therapeutic response so to refine not only the diagnostics but above all direct the best therapeutic choice.

The invention claimed is:

1. The pharmaceutical composition comprising a compound capable of functionally and selectively blocking the shorter isoform of Bruton's tyrosine kinase (BTK) having the amino acid sequence of SEQ ID NO: 2 and a chemotherapeutic drug for the treatment of epithelial tumours, wherein the compound capable of functionally and selectively blocking BTK comprises (a) a small interfering RNA (siRNA) or a short hairpin RNA (shRNA) targeting a 5'-untranslated region (5'-

UTR) (SEQ ID NO: 1) of a messenger RNA (mRNA) encoding a shorter isoform of Bruton's Tyrosine Kinase (BTK) having the amino acid sequence of SEQ ID NO: 2, wherein the shorter isoform does not contain amino acid residues 1-88 or 2-89 of the Bruton's Tyrosine Kinase (BTK) set forth in SEQ ID NO: 3; and (b) a pharmaceutically acceptable carrier.

2. The pharmaceutical composition according to claim 1, wherein the small interfering RNA (siRNA) comprises a double-stranded RNA comprising:
  (i) a sense polynucleotide strand having a nucleotide sequence length of from about 19 to about 23 nucleotides, wherein the sense polynucleotide strand is complementary to the 5'-untranslated region (5'-UTR) of the shorter isoform of the Bruton's Tyrosine Kinase (BTK) set forth in SEQ ID NO: 1; and
  (ii) an anti-sense polynucleotide strand that is complementary to the sequence of the sense polynucleotide strand.

3. The pharmaceutical composition according to claim 1, wherein the small hairpin RNA (shRNA) comprises:
  (i) a sense polynucleotide strand having a nucleotide sequence length of 19 to 23 nucleotides, wherein the sense polynucleotide strand is complementary to the 5'-untranslated region (5'-UTR) of the shorter isoform of the Bruton's Tyrosine Kinase (BTK) set forth in SEQ ID NO: 1;
  (ii) an anti-sense polynucleotide strand that is complementary to the sequence of the sense polynucleotide strand; and
  (iii) a polynucleotide linker sequence of sufficient length, wherein the polynucleotide linker sequence allows the sense polynucleotide strand and the anti-sense polynucleotide strand to fold over and hybridize to each other.

4. The pharmaceutical composition according to claim 3, wherein the small hairpin RNA (shRNA) is expressed by an expression vector.

5. The pharmaceutical composition according to claim 4, wherein the expression vector is a retroviral vector.

6. The pharmaceutical composition according to claim 1, wherein the siRNA or the shRNA does not affect expression of Bruton's Tyrosine Kinase (BTK) set forth in SEQ ID NO: 3.

7. The pharmaceutical composition according to claim 1, wherein the compound capable of functionally blocking the shorter isoform of Bruton's Tyrosine Kinase (BTK) having the amino acid sequence of SEQ ID NO: 2, wherein the shorter isoform does not contain amino acid residues 1-88 or 2-89 of BTK set forth in SEQ ID NO: 3 is at least one agent selected from the group consisting of LFM-A13, AVL-292, Ibrutinib, Dasatinib, Bosutinib, and a combination thereof.

8. The pharmaceutical composition according to claim 1, wherein said chemotherapeutic drug is at least one selected from the group consisting of an antimetabolite, a DNA-damaging agent, and a combination thereof.

9. The pharmaceutical composition according to claim 8, wherein the DNA-damaging agent is selected from the group consisting of topoisomerase I inhibitor, a topoisomerase II inhibitor, a platinum coordination compound, an alkylating agent, and a combination thereof.

10. The pharmaceutical composition according to claim 8, wherein said chemotherapeutic agent is selected from the group consisting of 5-fluorouracil (5-FU), oxaliplatin, and a combination thereof.

* * * * *